United States Patent [19]
Abreu et al.

[11] Patent Number: 5,315,513
[45] Date of Patent: * May 24, 1994

[54] SYSTEM FOR MODELLING MODERATE RESOLUTION ATMOSPHERIC PROPAGATION

[75] Inventors: Leonard W. Abreu, Chelmsford; Francis X. Kneizys, Burlington; Gail P. Anderson, Concord; James H. Chetwynd, Stoneham; Lex Berk, Medford; Larry Bernstein, Lexington; David Robertson, Bedford, all of Mass.

[73] Assignee: The United States of America as represented by the Secretary of the Air Force, Washington, D.C.

[*] Notice: The portion of the term of this patent subsequent to Dec. 24, 2008 has been disclaimed.

[21] Appl. No.: 784,487

[22] Filed: Oct. 29, 1991

[51] Int. Cl.$^5$ .................. G01V 1/00; G01W 1/10; G06F 15/54; G06G 7/48
[52] U.S. Cl. .................. 364/420; 356/432
[58] Field of Search ........... 364/420; 422/83, 98; 356/432, 437

[56] References Cited

U.S. PATENT DOCUMENTS

| | | | |
|---|---|---|---|
| 3,986,002 | 10/1976 | De Maio | 235/78 R |
| 4,010,357 | 3/1977 | Horner | 235/151.3 |
| 4,225,245 | 9/1980 | Roiret et al. | 356/437 |
| 4,521,861 | 6/1985 | Logan et al. | 364/17 |
| 4,614,429 | 9/1986 | Johnson | 356/343 |
| 5,075,856 | 12/1991 | Kneizys et al. | 364/420 |

Primary Examiner—Roy N. Envall, Jr.
Assistant Examiner—Laura Brutman
Attorney, Agent, or Firm—Donald J. Singer; William G. Auton

[57] ABSTRACT

MODTRAN is a moderate resolution model and computer code used to predict atmospheric transmittance and background radiance in the microwave, infrared, visible and near ultraviolet spectral regions (0 to 50,000 $cm^{-1}$ or 0.2 m to infinity). The code maintains complete compatibility with LOWTRAN 7, specifically, MODTRAN retains all of the capabilities of the LOWTRAN 7 model. Both codes contain the same six built-in model atmospheres; spherical refractive geometry, aerosol models, clouds (water and ice), rain attenuation and options to calculate single scattered solar/lunar radiance, solar/lunar irradiance and multiply scattered thermal and solar radiance. The MODTRAN code improves LOWTRAN'S spectral resolution from 20 to 2 $cm^{-1}$ full width/half maximum (fwhm) with an option to vary the resolution between 2 and 50 $cm^{-1}$ (fwhm). The band model parameters were formulated from the HITRAN line atlas for twelve atmospheric gases: $H_2O$, $CO_2$, $O_3$, $N_2O$, $CO$, $CH_4$, $O_2$, $NO$, $SO_2$, $NO_2$, $NH_3$, and $HNO_3$. These parameters were calculated for 1 $cm^{-1}$ bins from 0–17900 $cm^{-1}$ at 5 temperatures from 200 to 300 degrees K, all stored on an external data file which is accessed by the program.

6 Claims, 5 Drawing Sheets

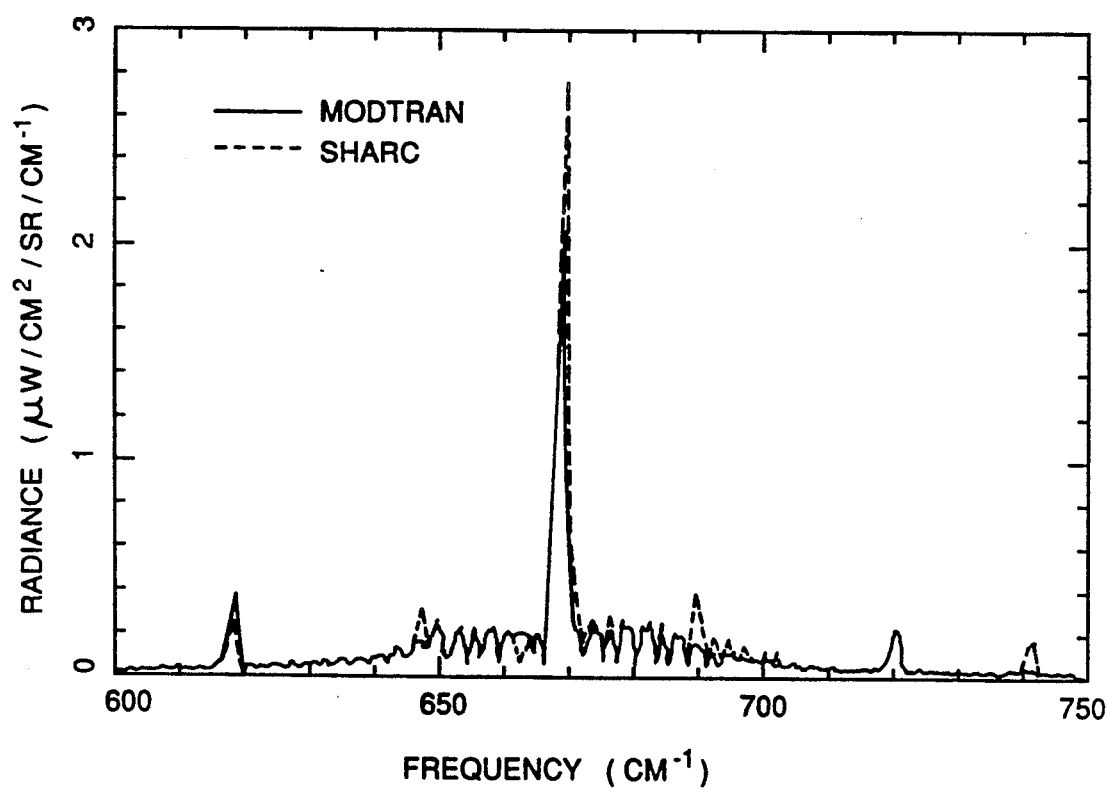

SYSTEM FOR MODELLING MODERATE RESOLUTION ATMOSPHERIC PROPAGATION

STATEMENT OF GOVERNMENT INTEREST

The invention described herein may be manufactured and used by or for the Government for governmental purposes without the payment of any royalty hereon.

REFERENCE TO MICROFICHE APPENDIX

Reference is made to the microfiche appendix which contains 5 sheets and 471 frames of the MODTRAN source code.

BACKGROUND OF THE INVENTION

The present invention relates generally to systems which calculate the effects of the atmosphere on the transmission of radio and optical beams, and more specifically to a moderate resolution propagation model of the earth's atmosphere. This model can be used for predicting atmospheric transmittance and background radiance from 0 to 50,000 $cm^{-1}$ at a resolution of 2 $cm^{-1}$.

The interest in atmospheric transmittance and background radiance along with the associated subject of astronomical refraction goes back to Laplace. With the advent of large telescopes and phase array radar systems, this interest has become ubiquitous, since the output signals of these systems experience attenuation due to atmospheric particles, water vapor and other gases along the viewing path.

The transmittance and radiance along a path through the atmosphere depend upon the total amount and the distribution of the absorbing or scattering species as well as the variation of pressure and temperature along the path. The integrated amount of absorber or scatterer along a path is known by various names, including "column density," "equivalent absorber amount," and "air mass." While the term "air mass" applies specifically to the total amount of gas along the path, it will be used here to refer loosely to the integrated amounts for all the different species relative to the amount for a vertical path.

The task of ascertaining atmospheric transmittance and atmospheric background radiance is alleviated, to some extent by the systems disclosed in the following U.S. Patents, the disclosures of which are incorporated herein by reference:

U.S. Pat. No. 4,010,357 issued to Joseph L. Horner;
U.S. Pat. No. 4,521,861 issued to Russell H. Logan et al;
U.S. Pat. No. 5,075,856 issued to Francis Kneizys et al; and
U.S. Pat. No. 3,986,002 issued to Dorian A. DeMaio.

Perhaps the most significant of the above-cited references is the Kneizys patent; which was filed on Jul. 17, 1989 as U.S. patent application Ser. No. 07/383,372 for the LOWTRAN 7 model of the atmosphere, which is discussed below. The Holyer reference discloses a satellite method for measuring sea surface temperature which utilizes LOWTRAN 5, which is a predecessor of the present invention.

In February of 1980, the Air Force Geophysics Laboratory of Hanscom Air Force Base, Massachusetts developed LOWTRAN 5, a Fortran computer code designed to calculate atmospheric transmittance and radiance for a given atmospheric path at low spectral resolution. The details of LOWTRAN 5 are described in a technical report by F. Kneizys et al entitled "Atmospheric Transmittance/Radiance; Computer Code LOWTRAN 5, AFGL-TR-80-0067," the disclosure of which is incorporated herein by reference. This report is available from the National Technical Information Service where it is identified as document number ADA088215.

In LOWTRAN 5, 6 and 7, the atmosphere is modeled as a set of spherically symmetric shells with discrete boundaries. The temperature, pressure, and absorber (gas and aerosol) densities are specified at the layer boundaries. Between boundaries, the temperature profile is assumed linear while the pressure and densities are assumed to follow exponential profiles.

LOWTRAN 6 was developed and described in August 1983 in a technical report entitled "Atmospheric Transmittance/Radiance; Computer Code LOWTRAN 6, AFGL-TR-83-0187," the disclosure of which is incorporated herein by reference. This report is available from the National Technical Information Service, where it is identified as document number ADA137796.

LOWTRAN 6 was an improvement over the previous model LOWTRAN 5, which assumed that the index of refraction was constant between layer boundaries. LOWTRAN 6 assumes a continuous profile for the refractive index, with an exponential profile between layer boundaries. It is more accurate than the previous models and works for all paths.

The LOWTRAN 7 model and computer code calculates atmospheric transmittance and background radiance for a given atmospheric path at low spectral resolution. This version is an extension and update of the current code, LOWTRAN 6 (and its predecessors LOWTRAN 5, LOWTRAN 4, LOWTRAN 3 and LOWTRAN 2). All the options and capabilities of the LOWTRAN 6 code have been retained, but additional refinements have been added, as described below.

The LOWTRAN 7 code calculates atmospheric transmittance, atmospheric background radiance, single scattered solar and lunar radiance, direct solar irradiance, and multiple scattered solar and thermal radiance. The spectral resolution of the model is 20 $cm^{-1}$ (full width at half-maximum) in steps of 5 $cm^{-1}$ from 0 to 50,000 $cm^{-1}$ (0.2 um to infinity). A single parameter band model is used for molecular line absorption and the effects of molecular continuum-type absorption; molecular scattering, aerosol and hydrometeor absorption and scattering are included. Refraction and earth curvature are considered in the calculation of the atmospheric slant pat and attenuation amounts along the path. Representative atmospheric, aerosol, cloud, and rain models are provided in the code with options to replace them with user-provided theoretical or measured values.

In view of the foregoing discussion, it is apparent that there remains an ongoing need to obtain refined estimates of atmospheric transmittance and background radiance, and that state-of-the-art methods are literally adapted for use almost as fast as they are developed by users that include the United States Air Force and other DOD agencies. The present invention is intended to satisfy that need.

SUMMARY OF THE INVENTION

The present invention is implemented in a computer program entitled MODTRAN. MODTRAN is a moderate resolution model of the earth's atmosphere and computer code used to predict atmospheric transmittance and background radiance in the microwave, infrared, visible and near ultraviolet spectral regions (0 to 50,000 cm$^{-1}$ or 0.2 um to infinity). The code maintains complete compatibility with LOWTRAN 7. MODTRAN retains all of the capabilities of the LOWTRAN 7 model. Both codes contain the same six built-in model atmospheres, spherical refractive geometry, aerosol models, clouds (water and ice), rain attenuation and options to calculate single scattered solar/lunar radiance, solar/lunar irradiance and multiply scattered thermal and solar radiance.

The MODTRAN code improves LOWTRAN's spectral resolution from 20 to 2 cm$^{-1}$ full width/half maximum (fwhm) with an option to vary the resolution between 2 and 50 cm$^{-1}$ (fwhm). The band model parameters were formulated from the HITRAN line atlas for twelve atmospheric gases: $H_2O$, $CO_2$, $O_3$, $N_2O$, CO, $CH_4$, $O_2$, NO, $SO_2$, $NO_2$, $NH_3$, and $HNO_3$. These parameters were calculated for 1 cm$^{-1}$ bins from 0–17900 cm$^{-1}$ at 5 temperatures from 200° to 300° K. The source code for MODTRAN is presented in the microfiche appendix. MODTRAN is usable on almost all data processor systems which are capable of operating with FORTRAN (i.e. most FORTRAN 77 compilers) and determines: atmospheric transmittance, atmospheric background radiance, single scattered solar and lunar radiance, direct solar radiance, and multiple scattered solar and thermal radiance. It may be used with external sensor systems which provide either known meteorological atmospheric data (temperature, pressure and density, etc.) or may use one of six internal reference atmospheric models to estimate these conditions as a function of altitude.

In operation MODTRAN may rely on physical sensors to provide weather data as input in a determination of atmospheric transmittance and background radiance to an infrared system, or a system analogous to the U.S. Navy's satellite temperature measurement system of the above-cited Holyer patent. The present invention can be regarded as a process for providing a moderate resolution propagation model and for predicting atmospheric transmittance and background radiance from 0 to 50,000 cm$^{-1}$ at a resolution of 2 cm$^{-1}$. This spectral resolution is ten times better than provided by the LOWTRAN 7 system. The process begins with an inputting step in which desired choices are made to define conditions under which the atmospheric transmittance and background radiance will be predicted. These conditions include: a choice of model atmosphere, a path of interest through the atmosphere, a spectral region of interest, and a level of spectral resolution that can range between about 20 and 2 cm$^{-1}$.

The process continues with a calculating step in which the atmospheric transmittance and background radiance is calculated. Finally, the process ends with an output step in which the atmospheric transmittance and background radiance is output along with the conditions selected in the input step.

In one embodiment of the invention, the calculating step is performed using a computer which contains a plurality of reference atmospheres which each define atmospheric temperature, pressure and density a a function of altitude. The computer serves as a means for calculating atmospheric transmittance and atmospheric background radiance and may function without external sensors (which provide measured values of temperature, pressure and density).

It is a principal object of the present invention to provide a moderate resolution propagation model for predicting atmospheric transmittance and background radiance to users of systems that include uv, visible, microwave and infrared tracking systems, communication systems, and satellite weather sensing systems.

It is another object of the present invention to provide a refined estimate of transmittance and multiple scattered radiation using an atmospheric data base that includes molecular profiles for thirteen minor and trace gases, and six reference atmospheric models that define temperature, pressure and density, as a function of altitude, and a number of models for the atmospheric aerosols, clouds and rain.

It is another object of the present invention to calculate the effects of weather on the transmission of infrared and optical beams.

These objects together with other objects, features and advantages of the invention will become more readily apparent from the following detailed description when taken in conjunction with the accompanying drawings wherein like elements ar given like reference materials throughout.

DESCRIPTION OF THE DRAWINGS

FIG. 8 is a chart of MODTRAN and SHARC predictions of the 15 micron $CO_2$ band for a 60 km path.

DETAILED DESCRIPTION OF THE PREFERRED EMBODIMENT

The present invention includes a moderate resolution propagation model of the earth's atmosphere. This model can be used for predicting atmospheric transmittance, background radiance, single scattered solar and lunar radiance, direct solar or lunar irradiance, and multiple scattered solar and thermal radiance. The spectral resolution of the model is 2 cm$^{-1}$ (full width at half-maximum) in steps of 1 cm$^{-1}$ from 0 to 50,000 cm$^{-1}$ (0.2 um to infinity).

The present invention is implemented in the computer code in the microfiche appendix, which can be run on any computer capable of operating in FORTRAN. This new code is called MODTRAN. The LOWTRAN transmittance model and associated subroutines have been fully integrated into MODTRAN, and all the LOWTRAN 7 options, i.e., aerosol models, atmospheric paths, transmittance/radiance, user-specified data, etc., have been maintained. Band model parameters have been formulated from the HITRAN line atlas for twelve atmospheric molecules: $H_2O$, $CO_2$, $O_3$, $N_2O$, CO, $CH_4$, $O_2$, NO, $SO_2$, $NO_2$, $NH_3$ and $HNO_3$. They were calculated for 1 cm$^{-1}$ bins from 0–17,900 cm$^{-1}$ and at five temperatures from 200 to 300 degrees K. These parameters are stored on an external data file (tape) which is accessed by the program. The transmittance is calculated with an equivalent-width formulation that takes into account the finite spectral width of each interval and the finite number of lines contained therein.

Note that the software and instructions for the MODTRAN package (as well as the HITRAN data base and LOWTRAN 7) are available from:
National Climatic Data Center, NOAA,
Environmental Data Services,
Federal Building,
Asheville, N.C. 28801
(704) 259-0272

Figure 1:
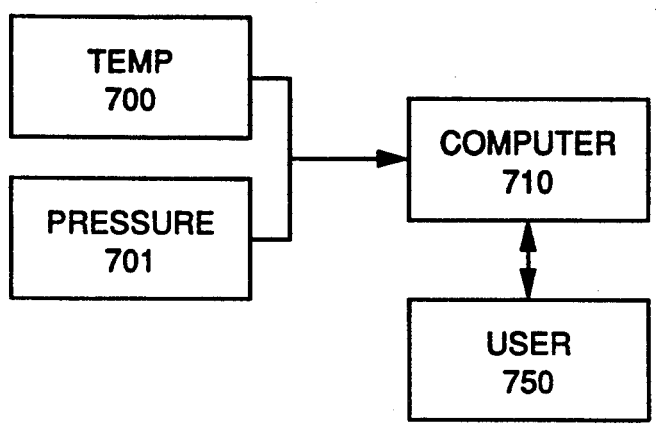
FIG. 1 is a block diagram of a sensor system which uses the present invention.

The disclosure of this commercially-available information is specifically incorporated by reference into this patent, and is implemented using the source code of the microfiche appendix, and the equipment of FIG. 1. This source code is usable with any system which uses a FORTRAN 77 compiler, and is immediately applicable to such systems which currently are using LOWTRAN 5, such as that of the above-cited Holyer patent.

The reader's attention is now directed towards FIG. 1 which is a block diagram of a system which uses the present invention. The system of FIG. 1 includes: a plurality of external sensors 700 and 701; a computer 710, and a host system 750 which is making use of the present invention.

The computer 710 can be any conventional system which includes a FORTRAN 77 compiler, and which is electrically connected with the external sensors 700 and 701 along with the host system 750. As discussed above, the computer 710 produces an estimate of: atmospheric transmittance; atmospheric background radiance; single and scattered solar and lunar radiance, direct solar irradiance; and multiple scattered solar and thermal radiance for slant angles used by the host system 750. As mentioned above, when the computer 710 is loaded with the MODTRAN program it can make these calculations using an atmospheric data base which includes molecular profiles for thirteen minor and trace gases, and six reference atmospheres which define atmospheric temperature, pressure and density as a function of altitude.

The user block 750 in FIG. 1 can be the data terminal of any sensor system (such as that of the Holyer patent) or communication system which transmits signals through the atmosphere. Such systems can greatly benefit from the use of MODTRAN. When they input their projected slant angles into the computer 710, they receive in return the estimates of atmospheric transmittance and background radiance, which affect such transmitted signals by different amounts Phased array radar systems that attempt to track remote orbiting objects and determine their radar cross sections can benefit by such estimates when they are aware of the effect of the atmosphere on target echo return signals.

Creation of this new code, MODTRAN, includes the development and integration of a completely new set of band models for calculating transmittance. The increased spectral resolution is achieved using an approach developed in a previous effort which resulted in a 5 cm$^{-1}$ option to LOWTRAN 5. In this approach, band model parameters were calculated from the HITRAN database and used to determine the equivalent width of the absorbing molecular gases in 5 cm$^{-1}$ spectral intervals. "HITRAN" means a compilation of atmospheric gas parameters which have been compiled in a data base and stored in a computer code by Phillips Laboratory of Hanscom AFB, MA. One of the reasons for MODTRAN's enhanced performance over the LOWTRAN system is the use of the HITRAN data base. In the present work, the band model parameters are calculated in 1 cm$^{-1}$ intervals. The molecular transmittance calculation for each bin has three elements.

Figure 2:
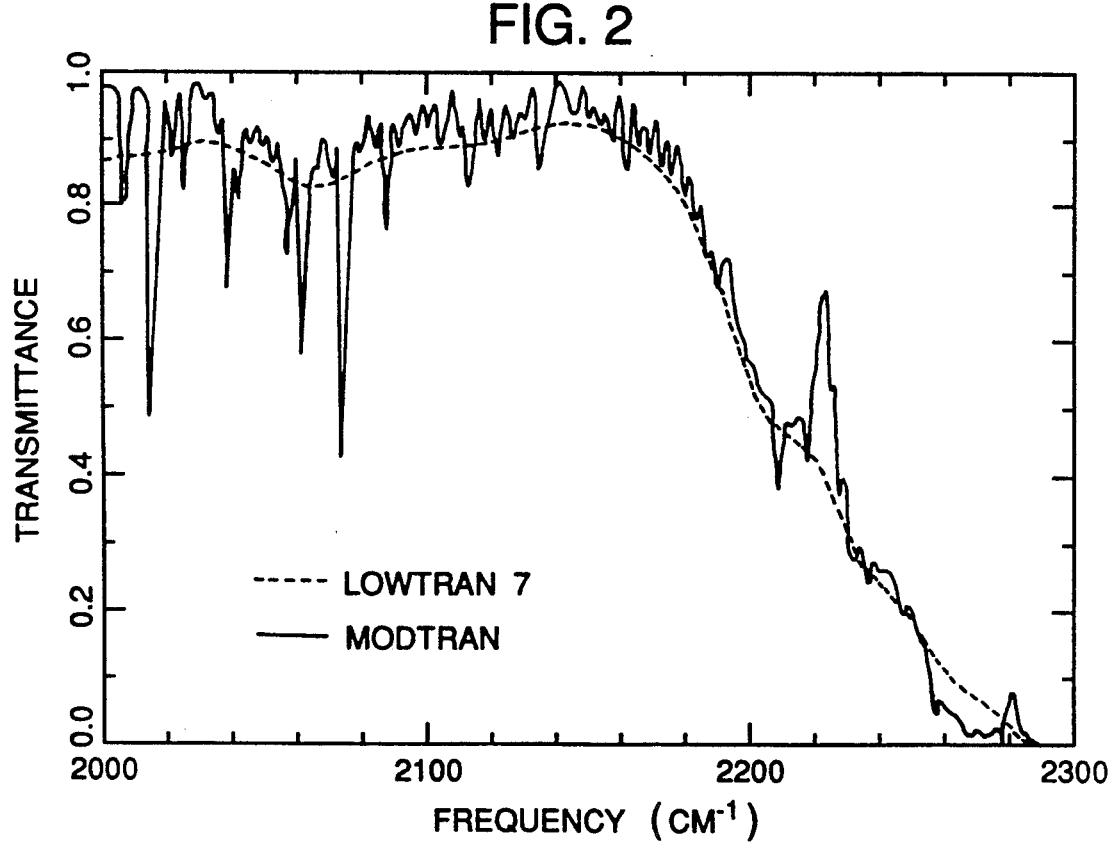
FIG. 2 is a chart comparing LOWTRAN 7 and MODTRAN predictions for atmospheric transmittance for a slant path from 5 to 10 km at 15 degrees.

The reader's attention is now directed towards FIG. 2, which is a chart of predicted atmospheric transmittance for a slant path of 5 to 10 km at 15 degrees through the U.S. standard atmosphere with no haze. Note that the comparison of MODTRAN and LOWTRAN 7 calculations shown in FIG. 2 illustrates the increased spectral resolution. The figure shows the transmittance calculated at 2 and 20 cm$^{-1}$ resolution for a low altitude slant path through the US Standard Atmosphere. The 2 cm$^{-1}$ curve results from the internal triangular slit function, and the 20 cm$^{-1}$ curve is the regular LOWTRAN 7 result calculated in 5 cm$^{-1}$ steps.

As shown in FIG. 2, the Voigt lineshape of an "average" line is integrated over the 1 cm$^{-1}$ interval. When a bin contains more than one line of a given species, the lines are assumed to be randomly distributed with statistical overlap. Finally, the contribution from lines whose centers are in nearby bins is calculated as a molecular "continuum" component. The other LOWTRAN components, which have insignificant spectral structure at 1 cm$^{-1}$, are calculated at their 5 cm$^{-1}$ increments and interpolated to arrive at the total transmittance for each interval. The calculational grid consists of non-overlapping 1 cm$^{-1}$ bins, which are degraded to the desired spectral resolution with an internal triangular slit function. Since these bins are square and non-overlapping, the nominal spectral resolution of MODTRAN is reported as 2 cm$^{-1}$ (FWHM).

The new MODTRAN subroutines are written in portable ANSII standard FORTRAN and constructed so that their interfacing with LOTRAN 7 minimizes coding changes. These additional elements do not interfere with the regular operation of LOWTRAN 7; rather they represent an additional capability for higher spectral resolution. All the usual LOWTRAN options like aerosol models, path options, multiple scattering model, user-specified profiles, etc., have been maintained. The large amount of molecular data required for the increased spectral resolution has necessitated using an external data file or band model tape.

MODTRAN is an improved version of LOWTRAN 7 with six additional subroutines that provide the increases spectral resolution. The input data sequence for MODTRAN is identical to LOWTRAN 7's except for two modifications, an additional parameter on Cards 1 and 4. A logical parameter, MODTRAN, has been added to the front end of CARD 1, and the input to CARD 4 has been changed to integer format with a resolution parameter, IFWHM, added. MODTRAN includes a switch which when set to F (false) causes the regular LOWTRAN 7 to be run and when set to T (true) activates MODTRAN. The parameter IFWHM, which is only read if MODTRAN is true, specifies the full width at half maximum, FWHM, of an internal triangular slit function.

MODTRAN and LOWTRAN 7 differ in their approaches to calculating molecular transmittance. For several different spectral intervals LOWTRAN 7 uses a one-parameter band model (absorption coefficient) plus molecular density scaling functions. The MODTRAN band model uses three temperature-dependent parameters, an absorption coefficient, a line density parameter and an average linewidth. The spectral region is partitioned into 1 cm$^{-1}$ bins for each molecule. Within each bin, contributions from transitions whose line centers fall within the bin are modeled separately from nearby lines centered outside of that bin, FIG. 3. The absorption due to lines within the bin is calculated by integrating over a Voigt line shape.

Figure 3:
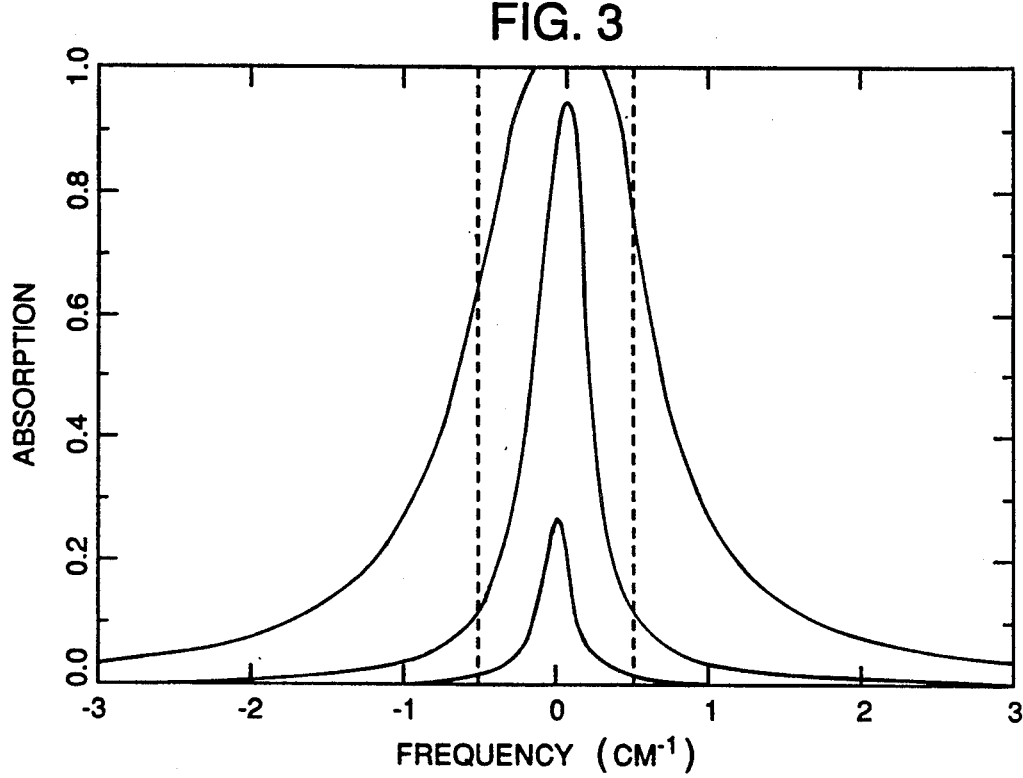
FIG. 3 is a chart of absorption from Lorentzian lines with optical depths of 0.1, 1 and 10.

FIG. 3 is a chart of predicted absorption from Lorenzian lines with optical depths of 0.1, 1, and 10. The halfwidth was set to 0.1 cm$^{-1}$. In the Band Model Transmittance Formulation, absorption from line centers (segment of curves falling within the spectral bin denoted by the dashed lines) is modeled separately from absorption due to line tails (outside the dashed lines).

The k-distribution method, which is used in LOWTRAN 7's multiple scattering treatment to correct for averaging over large spectral intervals, is not used in the MODTRAN version. Because three (monochromatic) k values are used for the 5 cm$^{-1}$ steps of LOWTRAN 7, the 1 cm$^{-1}$ MODTRAN steps provide an equivalent accuracy for the multiple scattering option.

MODTRAN is better suited than LOWTRAN for atmospheric paths which lie completely above 30 km. This is due to the integration over the Voigt lineshape combined with the explicit temperature and pressure dependencies of the band model parameters. The Voigt lineshape is necessary at these altitudes because the Doppler linewidth is greater than the Lorentz. The 20 cm$^{-1}$ versions of LOWTRAN suffer because they use a single set of band model parameters (nominally sea level at 296 K) coupled with spectrally independent scaling functions for the molecular densities. It is also noted that, for paths which lie completely above 60 km, another problem arises: many of the molecules are no longer in local thermodynamic equilibrium (LTE). This means that the strengths of some molecular bands can no longer be determined from the ambient temperature. MODTRAN gives reasonable results for those bands which are in LTE; the problem is identifying those spectral regions which are not LTE.

Figure 4:
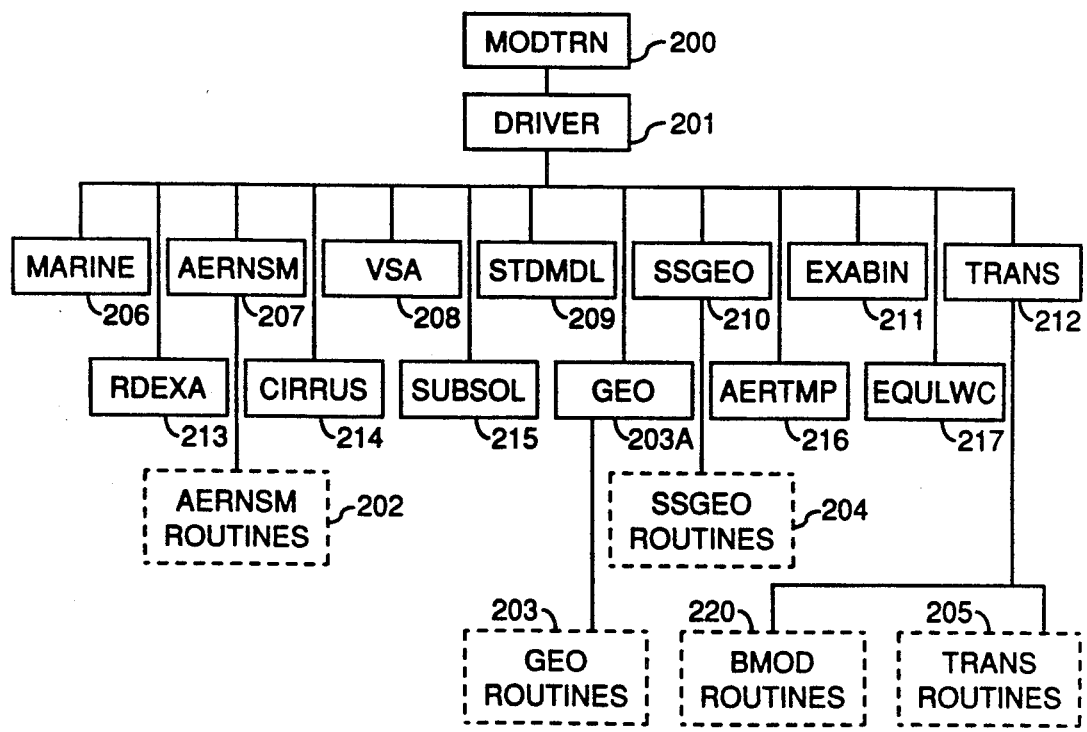
FIG. 4 is a block diagram of the computer subroutines in the MODTRAN computer model.

The reader's attention is now directed towards FIG. 4, which is a block diagram of the main program MODTRAN 7. This figure indicates that MODTRAN is composed of a total of twenty modules of subroutines 200-220, which are identified below in table 1, and described in further detail below.

The first subroutine 201 is the main driver program. This program reads the control cards input into the FORTRAN computer by the user, and initiates all other subroutines as directed by the user.

The MARINE subroutine 206 determines aerosol extinction and absorption coefficients for the Navy maritime model; the boxes enclosed by dashes are modules of subroutines for the calculations of non-standard models, air mass geometry, single scattering geometry and transmittance. The first of these AERNSM 207, defines a model atmosphere, aerosol profile and cloud profile. The characteristics of the model atmosphere of the AERNSM subroutine are defined in Table 2 of the above-cited Kneizys patent.

The GEO subroutine 203 is a set of air mass subroutine which calculates attenuator amounts for a particular slant path selected by the user. The SSGEO subroutine 204 obtains attenuator amounts from scattering points along a chosen optical path to an extraterrestrial source.

The TRANS set of subroutines 205 calculates transmittance, atmospheric radiance, and solar/lunar scattered radiance for a slant path. It also evaluates vertical profiles of optical quantities required for multiple scattering calculations.

The VSA subroutine 208 is a vertical structure algorithm of aerosol extinction and relative humidity for low visibility and low ceiling conditions. The subroutine labeled STDMDL 208 sets up scaled densities from the model atmosphere. The GEO routine 203 is the driver for the air mass subroutines and calculates attenuator amounts for a selected slant path.

The AERTMP subroutine 216 defines a temperature for each aerosol altitude region and the EQULWC subroutine 217 calculates the liquid water content of standard aerosols.

TABLE 1

| Description of MODTRAN Subroutines | |
|---|---|
| DRIVER | -Main driver program. Reads control cards. |
| MARINE | -Determines aerosol extinction and absorption coefficients for the Navy maritime model. |
| RDNSM | -Reads user input data when model 7 and VSA option are selected. |
| JOU | -Interpretive routine for JCHAR |
| CHECK | -Units conversion for pressure and temperature |
| DEFALT | -Chooses a stored atmospheric profile and interpolates default values for a specific altitude |
| CNVRT | -Accommodates uniform data input for model 0 or 7 |
| WVP | -Computes water vapor number density (mol cm-3) to accommodate "JCHAR" definitions for uniform data input |
| RDEXA | -IHAZE 7 or ICLD 11 triggers up to 4 regions of user input |
| RNSM | -Defines model atmosphere, aerosol profile and cloud profile |
| CIRRUS | -Generates altitude profiles of cirrus cloud density |
| RANDOM | -Calls machine-dependent function RANF, that is a uniform random number generator |
| VSA | -Army vertical structure algorithm of aerosol extinction and relative humidity for low visibility/low ceiling conditions |
| SUBSOL | -Calculates the subsolar point angles based upon time and day |
| STDMDL | -Sets up scaled densities from the model atmosphere |
| GEO | -Driver for air mass subroutines. Calculates attenuator amounts for the slant path. (GEO can be called by both SSGEO and in the main driver) |
| RMP | -Defines temperature for each aerosol altitude region |
| SSGEO | -Obtains attenuator amounts from scattering points along optical path to the extraterrestrial source |
| EXABIN | -Loads aerosol extinction, absorption and scattering |
| EQULWC | -Calculates liquid water content of standard aerosols |
| TRANS | -Calculates transmittance, atmospheric radiance, and solar/lunar scattered radiance for slant path. Sets up data for double exponential band model. Evaluates vertical profiles of optical quantities required for multiple scattering calculations. |

Further details on some of these subroutines are described in the above-cited Kneizys et al patent and need not be redescribed here, except to note that integration of the MODTRAN subroutines into LOWTRAN 7 was accomplished with minimal changes to the original code. The interface between the regular LOWTRAN 7 and the MODTRAN option is made through calls to two subroutines in the LOWTRAN 7 subroutine TRANS and one call in subroutine MSRAD. In TRANS, a single call to subroutine BMDATA reads the first necessary wavenumber block of band model parameters and calculates wavenumber independent quantities. For each wavenumber, calls to subroutine BMOD are made once for initialization and then additionally in the loop over atmospheric layers that calculates the molecular transmittance. In MSRAD, the call to FLXADD is replaced by a call to BMFLUX for the moderate-resolution option.

The new MODTRAN subroutines are described 850 lines of code.

Subroutine BMDATA is called once each calculation by subroutine TRANS. This subroutine opens the binary band model tape, makes the initial band model tape reads, and calculates wavenumber-independent quantities for subsequent use by subroutine BMOD.

After opening the band model tape, BMDATA reads the header information, advances the tape to the wavenumber block containing the initial frequency, IVI, and reads that block of data into common /BMDCOM/. If the requested spectral interval is totally outside of the band model tape range, the program simply performs a standard LOWTRAN 7 calculation.

For each atmospheric layer, wavenumber independent quantities are calculated in BMDATA and scored in the appropriate arrays for later use in BMOD. The quantities stored are $T/T_o$ in arrays WT and WTS, and temperature interpolation indices in arrays JJ, FF, JJS and FFS. Arrays affixed with the letter 'S' define parameters for the solar paths.

Subroutine BMLOAD (called BMOD) loads band model data for a single parameter set into the matrices SD, OD and ALFO.

BMTRAN is called by subroutine BMOD to calculate finite bin molecular transmittances. The curve-of-growth used in the statistical band model is based on the equivalent width of a single average line in a 1 $cm^{-1}$ interval. Band model parameters are calculated in BMOD for an equivalent homogeneous path, using the Curtis-Godson approximation.

As discussed in Subsection 4.1, the Voigt line shape is integrated over the interval. When the optical depth is less than 0.001, the weak line limit is used. Otherwise, the Voigt line shape is calculated from Equations (18)–(25).

BMERFU is called BMTRAN to calculate the finite bin width correction to the Voigt integral, Equations (21) and (22). For small non-negative z, the error function is calculated from the rational approximation given by Abramowitz and Stegun, Equation (7.1.26).(16) For large z, the error function is determined as a continued fraction derived from the asymptotic equation, Equation (7.1.23) of Reference 16.

BMFLUX is the moderate resolution version of the LOWTRAN 7 subroutine FLXADD. Called by MSRAD, BMFLUX is used to sum optical thicknesses to compute the diffuse thermal and solar flux contributions from a two-stream approximation, and to combine these fluxes in an adding routine which determines total upward and downward fluxes for each layer. The k-distribution method is not used in this fast version of FLXADD. Since the spectral intervals in the MODTRAN calculations are only 1 $cm^{-1}$, it treats these transmittances as monochromatic for the multiple-scattering fluxes. Thus, the molecular optical depth of a layer is calculated in MSRAD as a logarithm of molecular transmittances.

Modifications to LOWTRAN 7 have been kept to a minimum. As mentioned in Section 2, the switch MODTRAN has been added to /CARD1/. Only if MODTRAN is TRUE. are any of these changes activated.

Most of the routines from LOWTRAN 7 remain unchanged. A number of routines have been modified only that the blank common along with the labeled commons /CARD1/, /CARD4/, /SOLS/ and /TRAN/ have been changed. These routines are ABDTA, AEREXT, AERNSM, CIRRI8, CIRRUS, CLDPRF, DESATT, EQULWC, EXABIN, FLXADD, LAYVSA, PHASEF, RDEXA, RDNSM, RFPATH, SSRAD and VSANSM.

A number of routines have undergone minor modifications. Routines GEO and SSGEO were altered and STDMDL calculates actual rather than scaled molecular column densities when MODTRAN is .TRUE.. Finally, routine MSRAD computes molecular optical thicknesses and calls routine BMFLUX.

Significant changes were made to the MAIN. It has been split into two routines. The new MAIN consists of almost 1000 lines of introductory comments and a single call to the new subroutine DRIVER. DRIVER is the driver for MODTRAN and it contains all the executable statements from LOWTRAN 7's MAIN. In addition, it defines a pointer array called KPOINT that maps the HITRAN molecular labels into the LOWTRAN 7 labels. Also, DRIVER checks the spectral inputs.

The basic idea behind band model techniques used in MODTRAN is to determine a set of parameters from which transmittance over finite frequency intervals can be calculated. In MODTRAN, three band model parameters are used, an absorption coefficient, a line density and a line width. The absorption coefficient measures the total strength of lines in an interval. The line density is a line-strength weighted average for the number of lines in the interval, and the line width parameter is a line-strength weighted average line width.

MODTRAN uses a bin width of one wavenumber, $\Delta r = 1$ $cm^{-1}$. Line data from the HITRAN database and the line atlas, is used to calculate the band model parameters. The tape contains data on molecular lines in the frequency range 0 to 17900 $cm^{-1}$. For each molecule with lines whose centers fall within a given spectral bin, the temperature dependent absorption coefficients and line densities along with the line width parameter are stored for subsequent use in calculating molecular absorption; a single temperature-dependent absorption coefficient parameter is used t determine the tail contributions to each spectral bin from lines centered in nearby bins.

In the discussion that follows, the calculation of the molecular band model parameters is described, and the formatting of the data file is discussed in the third subsection. Formulas used to calculate the parameters are given, along with a discussion of their dependence on temperature and pressure.

Each frequency bin corresponds to a 1 $cm^{-1}$ interval and contains parameters for molecules with lines in that interval. The molecules for which band model parameters have been determined are: $H_2O$, $CO_2$, $O_3$, $N_2O$, $CO$, $CH_4$, $O_2$, $NO$, $SO_2$, $NO_2$, $NH_3$ and $HNO_3$.

The discussion that follows describes the invention in its broadest conceptual terms, and refers back to both FIGS. 1 and 4. The present invention may be described as a four step process of providing a moderate resulting model of the atmosphere that predicts atmospheric transmittance and background radiance. This process begins with the first step which includes selecting information that can include: the choice of model atmosphere, aerosols, path of interest through the atmosphere, scattering optics (presence of haze etc.), transmittance, radiance, and spectral range of interest. These selections can be made through the data terminal of the user block 750 in FIG. 1 and entail identifying the selection of which of: the six model atmospheres desired; the spectral region of interest 0 to 50,000 cm$^{-1}$; the choice of one of five reference temperatures (or an input from the temperature sensor 700); the optical path of interest; and the selection of level of spectral resolution (from 20 to 2 cm$^{-1}$). The next step includes performing spherical refractive geometry calculations over the chosen path of interest.

The third step includes the calculation of line of sight transmittance, thermal radiance, single scattered solar radiance, and multiple scattered solar radiance.

In MODTRAN, the molecular transmittance, $\tau$, from lines originating within a spectal bin, $\Delta\gamma$, is determined from an expression of the form $$\tau = \left( \frac{2}{\Delta\nu} \int_0^{\Delta\nu/2} e^{-Sub(\nu)} d\nu \right)^n \tag{1}$$

where $b(\gamma)$ is a line shape function, $\mu$ is the absorber amount, and S and n are functions of the absorption coefficient (S/d) and line density (1/d) band model parameters $$S = \frac{(S/d)}{(1/d)} \tag{2}$$

$$n = (1/d) \Delta\nu \tag{3}$$

A standard method for determining band model parameters was laid out by Goody in the standard text by him entitled "Atmospheric Radiation," which were published in 1964 by the Oxford University Press, the disclosure of which is incorporated herein by reference. As described by Goody expressions for the band model parameters have the form $$(S/d) = \frac{1}{\Delta\nu} \sum_{i=1}^{N} S_i \tag{4}$$

$$(1/d) = \frac{1}{\Delta\nu} \left( \sum_{i=1}^{N} \sqrt{S_i} \right)^2 / \sum_{i=1}^{N} S_i \tag{5}$$

The fourth step of the process includes receiving the output information which includes the identification of the parameters of step 1 and the results of the calculation of steps 2 and 3.

Further information on the mathematical background of the present invention is described in the technical report entitled "MODTRAN: A Moderate Resolution Model for LOWTRAN 7," by Alexander Berk et al. This report is incorporated by reference and is available at the Phillips Laboratory Library at Hanscom AFB, MA as catalogued under GL-TR-89-0122. Some of the information of this report is summarized briefly below.

The molecular absorption coefficients (S/d) (cm$^{-1}$ amagats$^{-1}$) are calculated at 5 reference temperatures: T=200, 225, 250, 275 & 300 K Linear interpolation is used to calculate absorption coefficients at temperatures between 200 and 300 degrees K. For temperatures below 200 and above 300K, the extreme values, (S/d) (T=200K) and (S/d) (T=300K), respectively, are used. The absorption band model parameters are calculated from the individual line strengths, $$(S/d) = \frac{1}{\Delta\nu} \sum_j S_j(T) \tag{6}$$

Here $S_j(T)$ is the integrated line strength at temperature T of the j'th line of molecule m in bin i. The line strength at an arbitrary temperature is scaled from the HITRAN line strength at its standard temperature, $T_s = 296$ K, by $$S_j(T) = \frac{Q_r(T_s)Q_v(T_s)}{Q_r(T)Q_v(T)} \tag{7}$$

$$\frac{1 - \exp(-hc\nu_j/kT)}{1 - \exp(-hc\nu_j/kT_s)} \exp\left( \frac{E_j}{k} \frac{T - T_s}{TT_s} \right) S_j(T_s)$$

where $Q_r$ and $Q_v$ are the rotational and vibrational partition functions, $E_j$ is the energy of the lower transition state, and $\gamma_j$ is the transition frequency. The constants are the speed of light (c), the Boltzman constant (k), and the Planck constant (h).

A collision broadened or Lorentz line width parameter $\gamma^o{}_c$ is defined at STP ($T_o=273.15$ K, $P_o=1013.25$ mbar). A single value can be stored because the pressure and temperature dependence of the Lorentz line width is easily modeled, $$\gamma_c(T, P) = \gamma_c^o \frac{P}{P_o} (T_o/T)^x \tag{8}$$

where the exponent x has been set to $\frac{1}{2}$ for all molecules except CO$_2$, for which $x=\frac{3}{4}$. The $\gamma^o{}_c$ band model parameter is calculated as a line strength weighted average over the tabulated Lorentz line widths $\gamma_{cj}(T_s)$ $$\gamma_c^o = (T_s/T_o)^x \left[ \sum_j \gamma_{cj}(T_s) S_j(T_s) \right] / \left[ \sum_j S_j(T_s) \right] \tag{9}$$

Like the absorption coefficients, the line density band model parameters (1/d) (cm) are calculated at the five reference temperatures and interpolated when used by the band model subroutines. The line density is defined by $$(1/d) = \frac{1}{\Delta\nu} \left( \sum_{j=1}^{N} S_j \right)^2 / \sum_{j=1}^{N} S_j^2 \tag{10}$$

This definition for the line spacing, which is derived in the appendix, produces a smaller value than the usual definition involving a sum over the square root of the line strengths. The new form results when account is taken of finite bin widths. The absorption of a line within a finite bin is less than its total line strength: this is consistent with a decreased value for (1/d).

The line tail parameters consist of line contributions from lines located outside of a given bin but within ±25 cm. The line tail absorption coefficient band model parameters C (cm$^{-1}$ amagat$^{-1}$) are determined by integrating the Lorentz line shape over this interval $$C = \frac{1}{\pi \Delta v} \sum_{k=i-25}^{i+25} (1 - \delta_{ki}) \left\{ \frac{[(S/d)\gamma_c]_k}{(k-i)^2 + \frac{1}{4}} f[(k-i)\Delta v] + \frac{[(S/d)\gamma_c]_k}{(k+i)^2 + \frac{1}{4}} f[(k+i)\Delta v] \right\} \quad (11)$$

where the delta function serves to exclude the $k-i$ term from the sum (i.e., the line center contribution), and $f[\Delta\gamma]$ is a lineshape form factor. The form factor is 1.0 within 25 cm$^{-1}$ of the line centers. Except for $H_2O$ and $CO_2$, tail contributions beyond 25 cm$^{-1}$ are assumed negligible and not included. The usual LOWTRAN 7 water continuum consists of tail contributions from lines located beyond 25 cm$^{-1}$ plus extrapolated (flat) values of this contribution within 25 cm$^{-1}$ (for smoothness). For $CO_2$, the continuum from FASCOD2 has been added to the C to account for the tail contributions from lines beyond 25 cm$^{-1}$, $$C \rightarrow C + v_i \tanh\left(\frac{hcv_i}{2kT}\right) \frac{T_s}{T} \overline{C}(v_i) \quad (12)$$

Here, $\overline{C}(\gamma_i)$ is the frequency interpolated value from FASCOD2's block data /FCO2/. For both $H_2O$ and $CO_2$, the value of C has also been reduced by an amount equal to its value at 25 cm$^{-1}$ from the line center since this contribution is included already in the continuum data.[14] The C is proportional to pressure (which arises from the Lorentz line width, Equation (8)).

$$C(P) = \frac{P}{P_o} C(P_o) \quad (13)$$

Because of the large amount of data, the band model parameters are stored in an external file that is written in binary format; this allows for quicker access during the calculation. Each entry corresponds to a 1 cm$^{-1}$ interval and contains a molecular parameter set. Since no data for molecules without lines in a given interval are stored, a parameter identifying the active species is included.

The first entry of a parameter set is the bin number i. From the bin number, the midpoint of the interval is calculated $$v_i = i \Delta v \quad (14)$$

and all lines whose centers fall in the half-opened interval $(\gamma_i - \Delta\gamma/2, \gamma_i + \Delta\gamma/2)$ contribute to bin i.

The molecular parameter set is identified by the parameter m. The HITRAN database convention is used for this labeling.

| m | 1 | 2 | 3 | 4 | 5 | 6 | 7 | 8 | 9 | 10 | 11 | 12 |
|---|---|---|---|---|---|---|---|---|---|---|---|---|
| molecule | $H_2O$ | $CO_2$ | $O_3$ | $N_2O$ | $CO$ | $CH_4$ | $O_2$ | $NO$ | $SO_2$ | $NO_2$ | $NH_3$ | $HNO_3$ |

The next entries in the parameter set are the molecular absorption coefficients (S/d) (cm$^{-1}$ amagats$^{-1}$) calculated at the five reference temperatures. These entries are followed by the STP Lorentz half width, $\sqrt[4]{°_c}$, multiplied by $10^4$ and stored as an integer. Line spacing parameters (1/d) for the five reference temperatures complete the line center parameter sets.

For line tails, each line contains data on one o two molecules. These line tail parameter sets use the same format as the line center parameter sets. Again, the first entry is the bin number i and the second entry is the molecule designation m. To recognize that these parameter sets denote line tail contributions, their molecule labels are offset by 12.

| m | 13 | 14 | 15 | 16 | 17 | 18 | 19 | 20 | 21 | 22 | 23 | 24 |
|---|---|---|---|---|---|---|---|---|---|---|---|---|
| molecule | $H_2O$ | $CO_2$ | $O_3$ | $N_2O$ | $CO$ | $CH_4$ | $O_2$ | $NO$ | $SO_2$ | $NO_2$ | $NH_3$ | $HNO_3$ |

The continuum parameters, C, are stored in place of the (S/d). Unless all tail contributions have been defined for frequency bin i, the molecular designation and continuum parameters for a second molecule follow the first on the same parameter set.

The band model transmittance formulation developed for the 5 cm$^{-1}$ option to LOWTRAN 5 has been used to create a moderate resolution option for LOWTRAN 7. The expression used to calculate molecular transmittance is based on a statistical model for a finite number of lines within a spectral interval, and is given by $$\tau = (1 - <W_{sl}>/\Delta v)^{<n>} \quad (15)$$

where $\tau$ is the transmittance, $<W_{sl}>$ is the Voigt single line equivalent width for the line strength distribution in a spectral interval, and $<n>$ is the path averaged effective number of lines in the bin $$<n> = \Delta v <1/d> \quad (16)$$

$<1/d>$ is the path averaged line spacing.

For large $<n>$ [(S/d) and $\Delta\gamma$ fixed], the transmittance simplifies to more recognizable exponential form, Beer's Law, given by $$\tau \rightarrow \exp(-<W_{sl}><1/d>) \quad (17)$$

For the relatively low temperatures encountered in the earth's atmosphere, the number of lines in a bin from a single molecular species is usually small so that the power law transmittance formulation is preferred.

There are many approximations available for calculating the equivalent width of a Voigt line shape; different ones are valid for different regimes, Doppler or collision broadening, weak line or strong line, etc. However, no single approximation is adequate for the range of pressures and optical path lengths encountered in atmospheric transmission calculations. Rather than incorporating different approximations, we directly evaluate the exact expression for the equivalent width of a single line in a finite spectral interval; ($<W_{sl}>$ is given by $$<W_{sl}> = \frac{\Delta \nu}{X_m} \int_0^{X_m} 1 - \exp\{-[S u/d]\sqrt{\ln 2/\pi}\ F(X,Y)/<\gamma_d/d>\}dX \quad (18)$$

$$F(X,Y) = \frac{Y}{\pi} \int_{-\infty}^{\infty} \frac{\exp(-T^2)\,dT}{Y^2 + (X-T)^2} \quad (19)$$

$$X_m = \frac{1}{2}\sqrt{\ln 2}\ <n>/<\gamma_d/d> \quad (20)$$

$$Y = \sqrt{\ln 2}\ <\gamma_c/d>/<\gamma_d/d> \quad (21)$$

where F(X,Y) is the Voigt line shape function, [S$\mu$/d] is the total optical depth, and $<\gamma_d/d>$ and $<\gamma_c/d>$ are the path averaged Doppler and collision broadened line shape band model parameters, respectively. To accurately calculate $<W_{sl}>$, we separate its contributions as shown:

$$<W_{sl}> = <W_{sl}^0> - <W_{sl}^1> \quad (22)$$

$$<W_{sl}^0> = \quad (23)$$

$$\frac{\Delta \nu}{X_m} \int_0^{\infty} 1 - \exp\{-[S u/d]\sqrt{\ln 2/\pi}\ F(X,Y)/<\gamma_d/d>\}dX$$

$$<W_{sl}^1> = \quad (24)$$

$$\frac{\Delta \nu}{X_m} \int_{X_m}^{\infty} 1 - \exp\{-[S u/d]\sqrt{\ln 2/\pi}\ F(X,Y)/<\gamma_d/d>\}dX$$

The tail contribution, $<W_{sl}^1>$ can easily be evaluated in terms of the error function since Xm>>Y for cases calculated with MODTRAN:

$$<W_{sl}^1> \approx \exp(-z^2) + \sqrt{\pi}\ z\ \text{erf}(z) - 1 \quad (25)$$

$$z = \frac{2}{<n>}\sqrt{[Su/d]<\gamma_c/d>/\pi} \quad (26)$$

To determine $<W_{sl}^0>$, an interpol between the Lorentz and Doppler limits is used. Based on an interpolation formula [Equations (25) and (26)], the Lorentz and Doppler equivalent widths are given by $$L = \frac{4}{4 + [Su/d]/<\gamma_c/d>} \quad (27)$$

$$D = \frac{2}{\ln 2}\ \frac{<\gamma_d/d>^2}{[Su/d]^2}\ \ln\left(1 + \frac{\ln 2}{2}\ \frac{[Su/d]^2}{<\gamma_d/d>^2}\right) \quad (28)$$

$<W_{sl}>$ is determined from the following interpolation formula which is a more numerically stable form of their formula:

$$<W_{sl}^0>^2 = \frac{[Su/d]^2}{<1/d>^2}\ \{1 - \quad (29)$$

$$(1-L)(1-D)/\sqrt{1 - L\,D\,(2-L)(2-D)}\ \}$$

Figure 5:
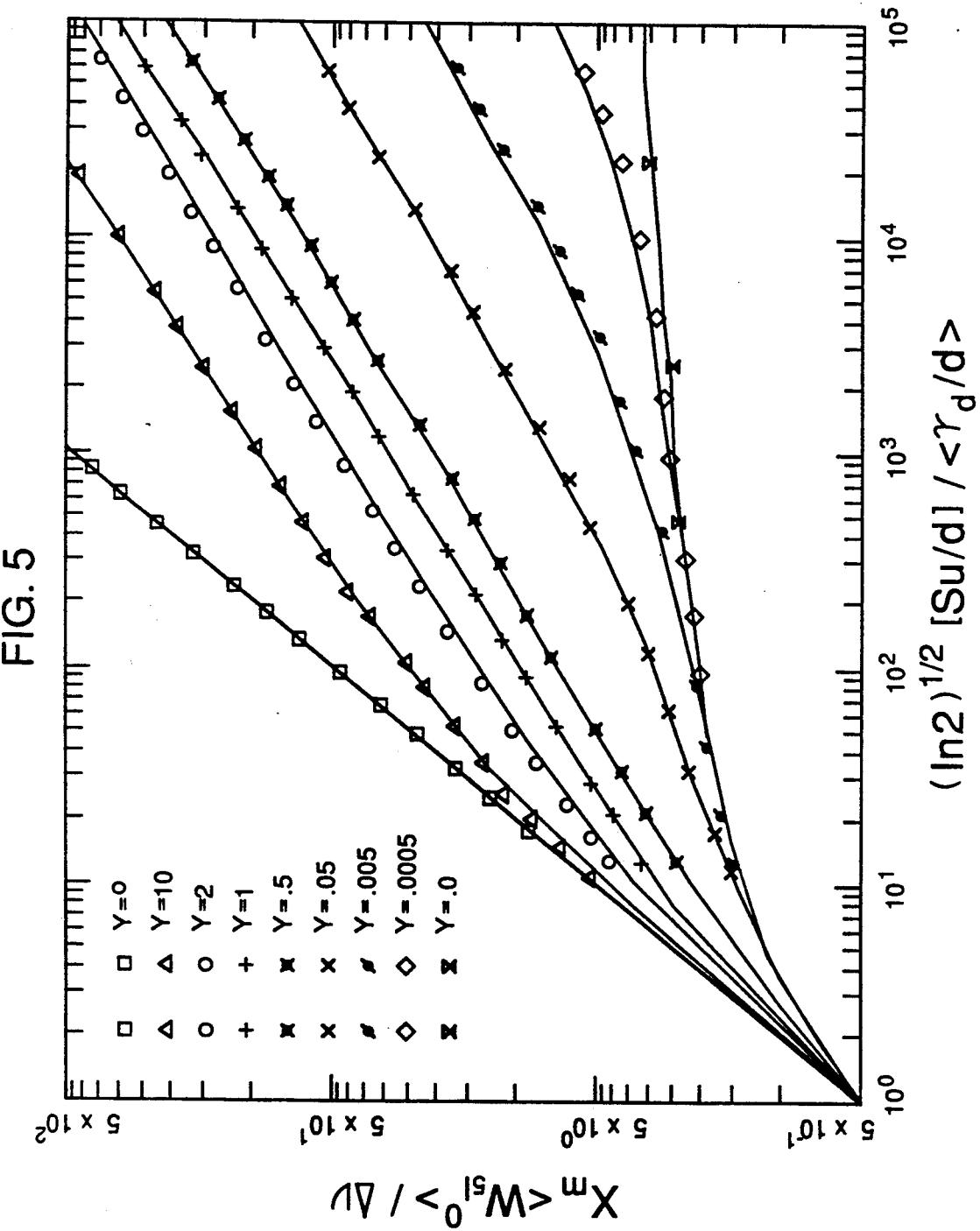
FIG. 5 is a chart of curves of growth of spectral lines with combined Doppler and Lorentz line broadening.

FIG. 5 shows a comparison of Equation (29) to exact calculations for the equivalent width of a single, isolated spectral line with a Voigt lineshape. The lowest curve is the pure Doppler limit and the highest curve is the Lorentz limit. The predictions of Equation (29) are shown as solid lines for the same values of the parameter Y, Equation 21. The overall agreement between the two families of curves illustrate the quality of the interpolation formula.

Both the LOWTRAN and MODTRAN programs have the option to calculate atmospheric and earth radiance. A numerical evaluation of the integral form of the equation of radiative transfer is used in the program. The emission from aersols and the treatment of aerosol and molecular scattering is considered only the zeroth order. Additional contributions to atmospheric emission from radiation scattered one or more times are neglected. Local thermodynamic equilibrium is assumed in the atmosphere.

The average atmospheric radiance (over a 20−cm$^{-1}$ interval) at the wavenumber, $\gamma$, along a given line-of-sight in terms of the LOWTRAN transmittance parameters is given by $$I(\nu) = \int_{\bar{\tau}_a{}^b}^1 d\bar{\tau}_a\ B(\nu, T)\bar{\tau}_s + B(\nu, T_b)\bar{\tau}_t{}^b \quad (30)$$

where the integral represents the atmospheric contribution and the second term is the contribution of the boundary, (for example, the surface of the earth or a cloud top) and $\bar{\tau}_a$=average transmittance due to absorption,
$\bar{\tau}_s$=average transmittance due to scattering,
$\bar{\tau}_t = \bar{\tau}_a \bar{\tau}_s$=average total transmittance,
$\bar{\tau}_a \bar{\tau}_t$=average totals transmittances from the observe to boundary,
$B(\nu,T)$=average Planck (blackbody) function corresponding to the frequency $\nu$ and the temperature T of an atmospheric layer.
$T_b$=temperature of the boundary.

The emissivity of the boundary is assumed to be unity.

The LOWTRAN band model approach used here assumes that since the blackbody function is a slowly varying function of frequency we can represent the average value of the radiance in terms of the average values of the transmittance and the blackbody function. $\bar{\tau}_a$, $\bar{\tau}_s$ and $\bar{\tau}_t$ vary from 1 to $\bar{\tau}_a$, $\bar{\tau}_s$, and $\bar{\tau}_t$ along the observer's line-of-sight.

The numerical analogue to Eq. (30) has been incorporated in the LOTRAN computer program. The numerical integration of the radiance along a line-of-sight for a given model atmosphere defined at N levels is given by $$I(\nu) = \sum_{i=1}^{N-1} (\bar{\tau}_a(i) - \quad (31)$$

$$\bar{\tau}_a(i+1))\,B\left(\nu, \frac{T(i) + T(i+1)}{2}\right)\left(\frac{\bar{\tau}_s(i) + \bar{\tau}_s(i+1)}{2}\right) +$$

$$B(\nu, T_b)\bar{\tau}_t{}^b.$$

Thus, the spectral radiance from a given atmospheric slant path (line-of-sight) can be calculated by dividing the atmosphere into a series of isothermal layers and summing the radiance contributions from each of the layers along the line-of-sight, that is, numerically evaluating Eq. (30).

Neglecting scattering, consider a three-layered atmosphere characterized by temperatures $T_1$, $T_2$, the and $T_3$. Let $\tau_1$, $\tau_2$ and $\tau_3$ be the transmittance from the ground to the boundaries of each of the layers respectively. Then from Eq. (31) the total downward spectral radiance for an observer on the ground (looking upwards) is given by $$I(\nu)\downarrow = (1\bar{\tau}_1(B(\nu,T_1)+\bar{\tau}_1-\bar{\tau}_2)B(\nu,T_2)+(\bar{\tau}_2-\bar{\tau}_3)B(\nu,T_3) \quad (32)$$

Similarly for an observer looking down from the top of the atmosphere the total upward spectral radiance is given by $$I(\nu)\uparrow = (1-\tau'_1)B(\nu,T_3)+(\tau'_1-\tau'_2)B(\nu,T_2)+(\tau'_2-\tau'_3)B(\nu,T_1)+\tau'_3B(\nu,T_b) \quad (33)$$

A comparison of Eqs. 32 and 33 shows that in addition to the boundary contributions to the total upward spectral radiance, the total downward and the total upward spectral radiances from the same atmospheric layers are not the same but depend on the position of the observer relative to a given atmospheric slant path.

Figure 6:
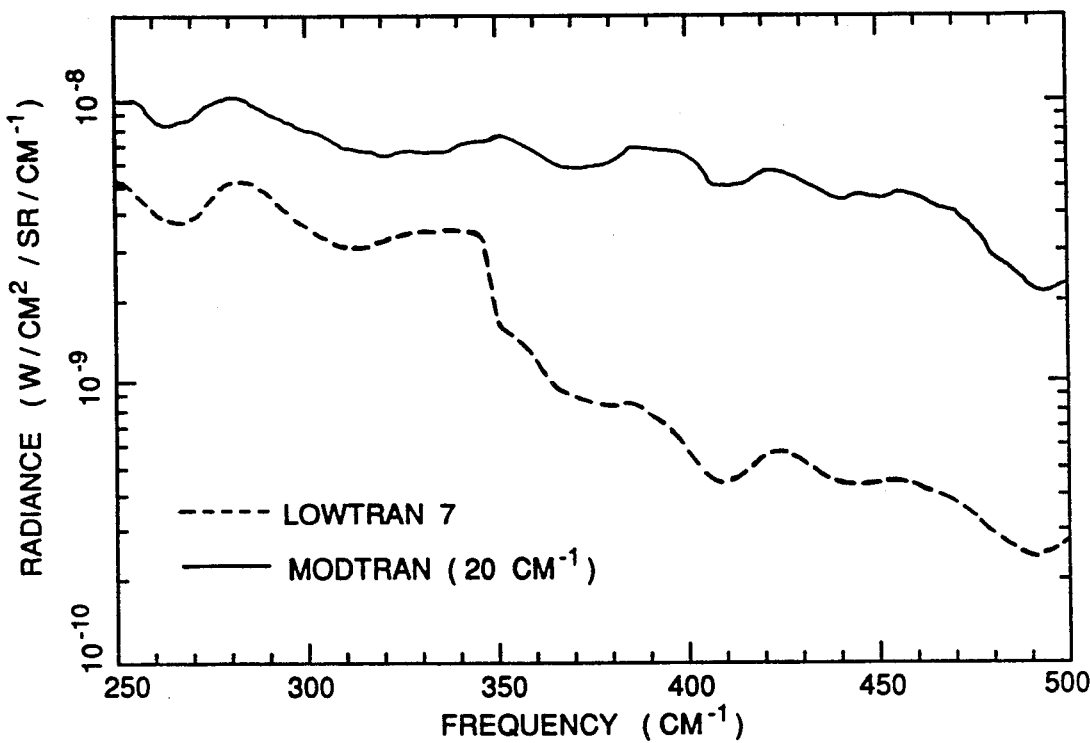
FIG. 6 is a chart of LOWTRAN 7 and MODTRAN predictions for radiation from the $H_2O$ rotational band and a 60 km path.
Figure 7:
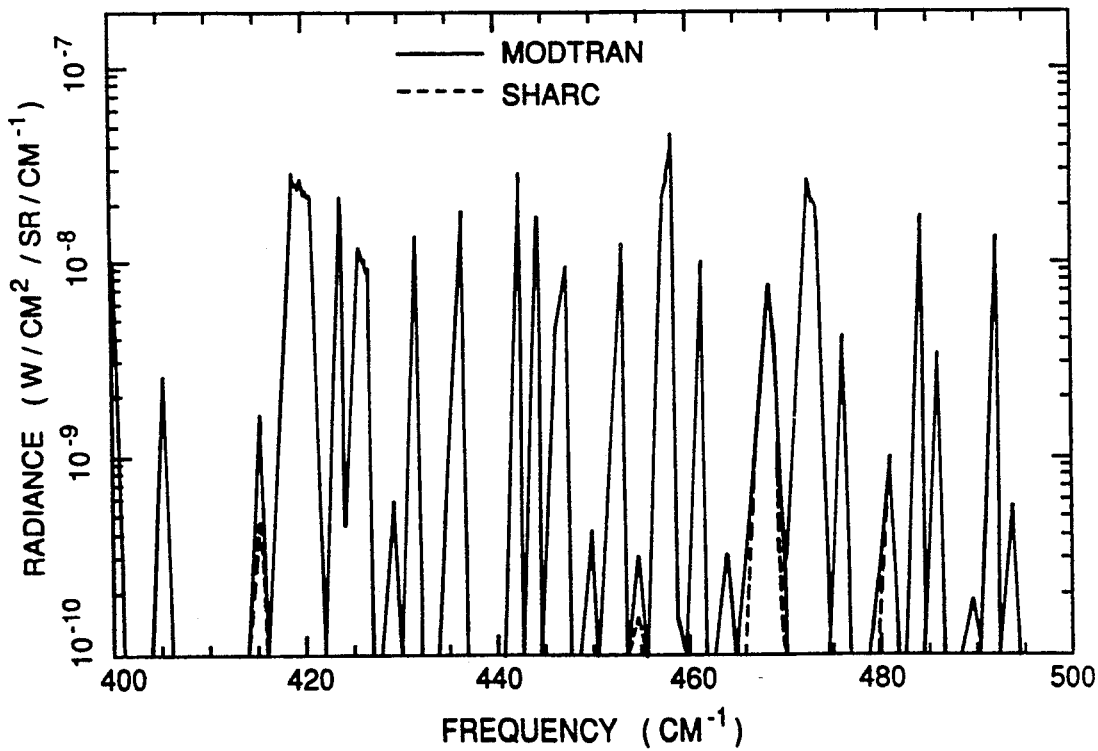
FIG. 7 is a chart of MODTRAN and SHARC predictions of $H_2O$ rotations for a 60 km path.

LOWTRAN 7 and MODTRAN differ in their approaches to handling molecular transmittance. Since the LOWTRAN model has been optimized for 296 K, sea level paths, LOWTRAN should not be used for atmospheric paths completely above 30 km. MODTRAN, on the other hand, uses a Voigt lineshape, which is applicable at higher altitudes. FIGS. 6–8 demonstrate MODTRAN'S high altitude capabilities. First, FIG. 6 shows that LOWTRAN 7 and MODTRAN do indeed predict vastly different radiances at higher altitudes. Radiation levels from $H_2O$ rotations along a 60 km limb path are shown. The LOWTRAN spectral radiances are much too low at these altitudes. To demonstrate that MODTRAN calculations are correct, validations have been performed against SHARC, the Strategic High Altitude Radiation Code. SHARC performs NLTE (non-local thermodynamic equilibrium) calculations from 60 to 300 km altitude. However, at 60 km, vibration state populations are essentially LTE and $H_2O$ rotations are always treated as LTE in SHARC, so comparisons between MODTRAN and SHARC should produce similar results. With a 60 km limb path, the two codes predict similar spectral radiances for $H_2O$ rotations (FIG. 7) and for the 15 m $CO_2$ band (FIG. 8) which is mostly LTE. The SHARC calculations were done at a spectral resolution of 0.5 cm$^{-1}$ and degraded to 1 cm$^{-1}$ (FWHM).

While the invention has been described in its presently preferred embodiment it is understood that the words which have been used are words of description rather than words of limitation and that changes within the purview of the appended claims may be made without departing from the scope and spirit of the invention in its broader aspects.

What is claimed is:

1. A moderate resolution atmospheric propagation model comprising:
   a host system which transmits signals through an atmosphere along selected slant angles and receives a first data stream in return, said host system outputting said first data stream along with a second data stream, said second data stream defining said slant angles; and
   a first means for calculating atmospheric transmittance and atmospheric background radiance which is electrically connected to said host system, said first calculating means receiving said first and second data streams from said host system and determining therefrom an estimate of atmospheric transmittance and atmospheric background radiance for said slant angles with a 2 cm$^{-1}$ spectral resolution that can range between 0 and 50,000 cm$^{-1}$ in steps of 1 cm$^{-1}$.

2. A moderate resolution atmospheric propagation model, as defined in claim 1, further comprising a second means for calculating single scattered solar and lunar radiance for said atmospheric radiance, said second calculating means being electrically connected with said host system.

3. A moderate resolution atmospheric propagation model, as defined in claim 2, further comprising a third means for calculating solar irradiance for said atmosphere, said third calculating means big electrically connected with said host system.

4. A moderate resolution atmospheric propagation model, as defined in claim 1, which further comprises:
   a computer memory which contains a plurality of reference atmospheres which each define atmospheric temperature, pressure and density as a function of altitude so that said first means for calculation atmospheric transmittance and atmospheric background radiance may function with and without external sensors which provide measured values of temperature, pressure and density.

5. A moderate resolution atmospheric propagation model, as defined in claim 4, wherein said computer memory includes an atmospheric data base which has separate molecular profiles for a plurality of minor and trace gases for altitudes that range between zero and one hundred kilometers, said minor and trace gases including: $H_2O$, $O_3$, $N_2O$, $CH_4$, $CO$, $O_2$, $CO_2$, $NO$, $NO_2$, $NH_3$, $HNO_3$ and $SO_2$.

6. A moderate resolution atmospheric propagation model, as defined in claim 5, wherein said computer memory has aerosol, rain and cloud models along with atmospheric scattering models and solar data stored therein.

* * * * *